United States Patent [19]

Morfeldt

[11] Patent Number: 5,900,411
[45] Date of Patent: May 4, 1999

[54] METHOD OF TREATMENT OF KAPOSI'S SARCOMA

[75] Inventor: Linda Morfeldt, Lidingö, Sweden

[73] Assignee: Astra Akiebolag, Sodertalje, Sweden

[21] Appl. No.: 08/564,124

[22] PCT Filed: Nov. 9, 1995

[86] PCT No.: PCT/SE95/01328

§ 371 Date: Aug. 15, 1996

§ 102(e) Date: Aug. 15, 1996

[87] PCT Pub. No.: WO96/14848

PCT Pub. Date: May 23, 1996

[30] Foreign Application Priority Data

Nov. 9, 1994 [SE] Sweden .................................. 9403861

[51] Int. Cl.$^6$ ...................................................... A61K 31/66
[52] U.S. Cl. ............................................................ 514/120
[58] Field of Search ............................................. 514/120

Primary Examiner—Jerome D. Goldberg
Attorney, Agent, or Firm—White & Case LLP

[57] ABSTRACT

Use of forscarnet in the prophylaxis and/or treatment of Kaposi's sarcoma.

12 Claims, No Drawings

METHOD OF TREATMENT OF KAPOSI'S SARCOMA

FIELD OF THE INVENTION

The present invention relates to a novel method for prophylaxis and for the treatment of Kaposi's sarcoma.

DEFINITIONS

The term "foscarnet" herein denotes phosphonoformic acid or physiologically acceptable salts thereof, for example FOSCAVIR®, the trade name for foscarnet sodium, which is trisodium phosphonoformate hexahydrate.

Dose figures given as mg/kg/day are to be interpreted as weight of active substance per body weight of the patient per day.

BACKGROUND OF THE INVENTION

There are four different types of Kaposi's sarcoma (KS): Classic KS, endemic African KS, KS associated with immunosuppressive therapy, and epidemic/HIV-AIDS related KS.

KS is the most common AIDS-related neoplasia and contributes to morbidity and mortality in AIDS patients. The majority of cases of epidemic KS is seen in homosexual males with immunodeficiency of clinical significance. KS is currently afflicting approximately 20 000 AIDS patients annually in the United States (AIDS Weekly, Sep. 12, 1994). Up to 40 per cent of homosexual men with AIDS eventually develop KS.

The cause of KS is not yet known. Epidemiological studies indicate that a sexually transmissible agent is a factor of pathogenetic importance (Beral, V. et al: Kaposi's sarcoma among persons with AIDS: a sexually transmitted infection?, Lancet 335: 123–128, 1990, and Elford, J. et al: Kaposi's sarcoma as a sexually transmissible infection: an analysis of Australian AIDS surveillance data. AIDS 7: 1667–1671, 1993).

KS appears as reddish or purple lesions preferentially on the skin and mucous membranes of he gastrointestinal tract. About 50 per cent of cases exhibit lesions in the mouth. In advanced cases of KS lymph nodes and parenchymatous organs such as lungs and liver are frequently involved.

The KS lesions are often the only visible sign of AIDS and lead to severe psycho-social problems for the patient. During the course of KS the cutaneous lesions may become painful and secondary oedema from lymph node involvement may cause grotesque swelling of different parts of the body. Bleedings or obstruction of the gastrointestinal tract or the lungs occurs in advanced cases of KS.

Characteristic histopathological features of KS tumors include interweaving bands of "spindle cells" and vascular structures embedded in a network of collagen and reticular fibers. The presence of extravasated blood cells and hemosiderin is also characteristic. Whether or not KS is a true malignancy or merely a hyperplasia of certain tissues has been debated for quite some time. The isolation of KS cells from a patient exhibiting all the characteristics of a true malignancy has now been reported. At the same time it was claimed that a transmissible agent is not necessary for the pathogenesis of KS (Gallo, R. C. at The International Conference on AIDS in Yokohama, August, 1994).

Spindle cells characteristic of KS have been isolated from blood of HIV-infected patients with KS and, remarkably, spindle cells have been isolated from a substantial proportion of HIV-infected homosexual men without any signs of KS (Gallo, R. C., ibid.). It might, therefore, be that KS can be diagnosed by the detection of markers in blood or secretions before visible lesions of KS appear in patients.

At present, there is no cure for KS or the immunodeficiency of HIV infection. The patients suffering from KS are currently offered chemotherapy, interferons, irradiation or different kinds of local treatment for palliation. Short remission and considerable side-effects limit the benefit of these therapeutic regimens. Continuous therapy is most often needed. Hair loss, nausea, vomiting, granulocytopenia with risk for bacterial infections, peripheral neuropathies and pulmonary problems are negative side-effects which significantly impair the quality of life of the patient.

Several studies have failed to show any significant anti-KS effect attributable to zidovudine, commonly known as AZT, which is an antiviral drug widely used against HIV-infection (Lane, HC et al.: Zidovudine in Patients with Human Immunodeficiency Virus Infection and Kaposi sarcoma, Ann Int Med 111, 41–50, 1989; de Wit et al.: Lack of activity of zidovudine in AIDS-associated Kaposi's sarcoma, AIDS 3: 847–850, 1989).

Foscarnet is an antiviral drug, which is presently being used in the treatment of patients infected with herpes simplex virus or cytomegalovirus. Foscarnet inhibits replication of herpesviruses in vitro including cytomegalovirus (CMV), herpes simplex virus types 1 and 2 (HSV-1, HSV-2), human herpesvirus 6 (HHV-6), Epstein-Barr virus (EBV), and varicella-zoster virus (VZV) as well as certain retroviruses, including the Human Immunodeficiency virus (HIV).

Foscarnet causes relatively few negative side-effects in patients as compared to cytostatics or interferons, the drugs presently being used in cases of KS.

SUMMARY OF THE INVENTION

It has been found according to the present invention that administration of foscarnet to human patients affected by KS results in long-term remission of KS. Patients have been free of relapse for long periods upon treatment comprising administration of foscarnet.

According to the present invention foscarnet can be administered parenterally by intravenous infusion of a solution of a physiologically acceptable salt of foscarnet, in particular the trisodium salt. Parenteral administration may also be intralesional. Alternatively, administration can be oral, topical or by inhalation. The formulations to be used for parenteral infusion are preferably formulated as sterile aqueous solutions of foscarnet. A preferred parenteral composition for intravenous infusion is as follows: Foscarnet (trisodium phosphonoformate hexahydrate) 24.7 mg, hydrochloric acid 2M for injection q.s., water for injection to 1.0 ml. Normally the commercially available pharmaceutical formulations of foscarnet will be used for treating Kaposi's sarcoma.

The doses to be used in the therapy of patients suffering from Kaposi's sarcoma according to the present invention are 10–2000 mg/kg/day, preferably 50–200 mg/kg//day.

Desirable serum levels of foscarnet in patients being treated according to the present invention are 50–1000 $\mu$M. Serum levels of foscarnet between 300–600 $\mu$M will be particularly desirable.

According to the present invention foscarnet can be administered during repeated periods interrupted by time intervals without administration of foscarnet.

One aspect of the present invention is that healing of Kaposi's sarcoma will contribute to significant improvement of quality of life particularly in patients suffering from AIDS.

Another aspect of the present invention is that the negative side-effects and long treatment time of the current treatment regimens can be avoided. Thus, the quality of life of the patients being treated with foscarnet according to the present invention is significantly better than for patients treated with cytostatics, interferon or irradiation.

Another aspect of the present invention is that foscarnet can be administrated to patients as a prophylactic agent against KS.

DETAILED DESCRIPTION OF THE INVENTION

The present invention provides the first demonstration that KS in humans can be treated utilizing foscarnet as an active agent.

The invention relates in different aspects to:
- a method for prophylaxis and/or treatment of KS in man comprising administration of a therapeutically effective dose of phosphonoformic acid or a physiologically acceptable salt thereof,
- the use of phosphonoformic acid or a physiologically acceptable salt thereof in the manufacture of a medicament for the prophylaxis and/or treatment of KS,
- a pharmaceutical formulation for the prophylaxis and/or treatment of KS comprising phosphonoformic acid or a physiologically acceptable salt thereof as active ingredient.

For the purpose of illustration only, the invention will be described in terms of the use of an intravenous solution of trisodium phosphonoformate. This illustration is not intended to limit the scope of the claims of the present invention as hereinafter set forth.

EXAMPLE 1

The method of treatment can be exemplified as follows: The patient with lesions attributable to KS was treated with foscarnet by intravenous infusions of FOSCAVIR® at a dose of 180 mg/kg/day for ten days. The KS lesions were recorded and documented before and repeatedly after treatment on a preformed template as well as by photography. The diagnosis of KS was histologically verified.

A 57-year old white homosexual man who was admitted to the hospital because of Pneumocystis carnii pneumonia (PCP). The initial CD4 cell count was $24 \times 10^6/l$. The patient manifested six nodular KS skin lesions and multiple lesions of the palate. He received a ten day course of foscarnet. Three new skin lesions were detected two weeks later. One month post treatment a partial regression of some of the lesions was noted and after that all the lesions gradually diminished. After four months of observation the nodular component of the lesions had resolved leaving brownish maculae. The lesions of the palate were hardly visible. Biopsy findings at this point indicated a parallel histological resolution. After 12 months all the skin lesions had almost completely resolved. At this time, however, the oral lesions began to recur. By month 15 the skin lesions remained unchanged but after 17 months three new lesions were noted and the initial ones had reappeared.

I claim:

1. A method of treatment of Kaposi's sarcoma in humans, comprising the administration to said humans of a therapeutically effective dose of phosphonoformic acid or a physiologically acceptable salt thereof.

2. A method according to claim 1 wherein phosphonoformic acid or a physiologically acceptable salt thereof is administered parenterally.

3. A method according to claim 1, wherein phosphonoformic acid or a physiologically acceptable salt thereof is administered intralesionally.

4. A method according to claim 1, wherein phosphonoformic acid or a physiologically acceptable salt thereof is administered intravenously.

5. A method according to claim 1, wherein phosphonoformic acid or a physiologically acceptable salt thereof is administered orally.

6. A method according to claim 1, wherein phosphonoformic acid or a physiologically acceptable salt thereof is administered topically.

7. A method according to claim 1, wherein phosphonoformic acid or a physiologically acceptable salt therof is administered by inhalation.

8. A method according to claim 1, wherein phosphonoformic acid is administered in the form of its trisodium salt.

9. A method according to claim 1 or 8, wherein phosphonoformic acid or a physiologically acceptable salt thereof is administered at a dose of 10–2000 mg/kg/day.

10. A method according to claim 1 or 8, wherein phosphonoformic acid or a physiologically acceptable salt thereof is administered at a dose of 50–200 mg/kg/day.

11. A method according to claim 1 or 10 wherein phosphonoformic acid or a physiologically acceptable salt thereof is administered in an amount sufficient to give a serum level of phosphonoformic acid in the range of 50–1000 $\mu$M.

12. A method according to claim 1 or 8, wherein phosphonoformic acid or a physiologically acceptable salt thereof is administered in an amount sufficient to give a serum level of phosphonoformic acid in the range of 300–600 $\mu$M.

* * * * *